United States Patent [19]

Taheri

[11] Patent Number: 5,916,817
[45] Date of Patent: Jun. 29, 1999

[54] METHOD FOR DETECTING DEEP VENOUS THROMBOSIS

[76] Inventor: Syde A. Taheri, 268 Dan Troy, Williamsville, N.Y. 14221

[21] Appl. No.: 08/919,468

[22] Filed: Aug. 28, 1997

[51] Int. Cl.$^6$ .................................................. G01N 33/537

[52] U.S. Cl. .......................... 436/501; 435/7.1; 435/7.92; 435/335; 436/811; 436/815; 128/666

[58] Field of Search ..................................... 436/501, 811, 436/815; 435/7.1, 7.92, 335; 128/666

[56] References Cited

U.S. PATENT DOCUMENTS 5,766,865   6/1998   Chen et al. ............................. 435/7.21

*Primary Examiner*—Laurie Scheiner
*Attorney, Agent, or Firm*—Hodgson, Russ, Andrews, Woods & Goodyear LLP

[57] ABSTRACT

A method for predicting the presence of deep vein thrombosis in a patient comprises measuring the concentration of soluble tumor necrosis factor receptor-1 in the venous blood of the patient and comparing it to an established baseline concentration. A concentration in the patients venous blood higher than the established baseline concentration is predictive of the presence of deep vein thrombosis.

1 Claim, No Drawings

METHOD FOR DETECTING DEEP VENOUS THROMBOSIS

BACKGROUND OF THE INVENTION

FIELD OF THE INVENTION

This invention relates to a screening method useful for the detection of deep vein thrombosis.

Deep vein thrombosis (DVT) is a relatively common and extremely serious disorder that may be potentially fatal since it may lead to pulmonary emboli. DVT is common in patients who are immobilized for relatively long periods of time as a result of a medical or surgical illness, or patients with multiple trauma or malignant diseases. It also occurs commonly in persons who are immobilized or of limited mobility as a result of being paraplegic or quadriplegic and may also develop in otherwise healthy persons, after prolonged sitting or immobilization.

Clinical recognition of deep vein thrombosis generally relies on methods that are useful for a confirmation diagnosis of DVT, but are generally unsatisfactory for screening purposes for various reasons.

SUMMARY OF THE INVENTION

It has now been found that the presence of deep vein thrombosis in a patient may be detected in a relatively simple and effective manner by measuring the concentration of soluble tumor necrosis factor receptor-1 present in a sample of the patients blood and comparing that concentration to an established baseline concentration of soluble tumor necrosis factor receptor-1. The presence of or development of deep vein thrombosis may then be predicted if the concentration of soluble tumor necrosis factor receptor-1 in the blood sample exceeds that of the established baseline.

Although it is not intended to be bound by a particular theory, it is postulated the production of cytokines, in particular the cytokine known as tumor necrosis factor-alpha (also known as cachetin), a cytotoxic protein produced by lymphocytes in the human body, plays an important role in the genesis of deep vein thrombosis and the evolution of this disease. Soluble tumor necrosis factor receptor 1 is generated by inflammatory cells during clot formation and is a surrogate marker for inflammatory diseases in which tumor necrosis factor plays an important role. Based on studies detailed hereinbelow, we have found that, in patients with deep vein thrombosis, the concentration of soluble tumor necrosis factor receptors is markedly increased and reflects the activity of inflammatory cells in deep vein thrombosis.

DETAILED DESCRIPTION OF THE INVENTION

The concentration of soluble tumor necrosis factor receptor 1 (p55) in a sample of blood may be determined by the assay procedure known as ELISA. The procedure is as follows:

a monoclonal antibody specific for the soluble tumor necrosis factor receptor 1 is pre-coated onto a microtiter plate.

Standards and samples are pipetted into the wells and any soluble tumor necrosis factor receptor 1 present is bound by the immobilized antibody.

After washing away any unbound substances, an enzyme-linked polyclonal antibody specific for soluble tumor necrosis factor receptor 1 is added to the wells.

After a wash to remove and unbound antibody-enzyme reagent, a substrate solution is added to the wells and color develops in proportion to the amount of soluble tumor necrosis factor receptor 1 bound in the initial step.

The color development is stopped and the intensity of the color is measured and compared to a standard.

Study Procedure

A study (approved by the Institutional Review Board) was carried out on 17 patients with deep vein thrombosis, including 4 cases of pulmonary emboli. The study group included 10 females and 7 males. The youngest patient in the group was 34 and the oldest was 74, with an average age of 45 years. Sixteen healthy volunteers, 8 female land 8 male, served as control subjects.

The symptoms among the 17 patients included leg pain (11), chest pain (4), swelling (15), shortness of breath (5) and varicose veins (2). The patients were examined with respect to blood chemistry, complete blood count, sedimentation rate, and rheumatoid factors. Ultrasound imaging and V/Q scans were used for diagnosis of deep vein thrombosis and pulmonary emboli. A blood sample (5 cc) was taken from each patient and assayed by the aforementioned ELISA method to determine the concentration of soluble tumor necrosis factor receptor 1 (p55) present in the sample.

The diagnosis by ultrasound imaging and V/Q scans for deep vein thrombosis and pulmonary emboli in the study group gave the following results:

Deep vein thrombosis and pulmonary emboli were present in:

| Location | No. Of patients |
| --- | --- |
| Right femoral vein | 3 |
| Left femoral vein | 4 |
| Left ilia-femoral vein | 1 |
| Right axillary vein | 1 |
| Pulmonary emboli | 4 |
| Calf vein | 2 |
| Bilateral femoral vein | 2 |

The assay for soluble tumor necrosis factor receptor-1 (p55) indicated an average normal concentration of 900 picograms/mL, the lowest being 544 pg/mL and the highest 1610 pg/mL. In the patients having diagnosed deep vein thrombosis or pulmonary emboli, the average concentration was 1965 pg/mL, the lowest being 797 pg/mL and the highest 4244 pg/mL. The concentration of soluble tumor necrosis factor receptor-1 (p55) was found to be highest in those patients where the presence of deep vein thrombosis was diagnosed as bilateral and those patients having a diagnosis of pulmonary emboli.

Based on the findings, it is considered that a baseline concentration of about 1000 pg/mL may be used for purposes of prediction of deep vein thrombosis so that if the concentration in a sample of venous blood of a patient is higher than that baseline concentration, the presence of deep vein thrombosis may be predicted.

What is claimed is:

1. A method for predicting the presence of deep vein thrombosis in a patient comprising the steps of:

a) obtaining a sample of venous blood from said patient;

b) measuring the concentration of soluble tumor necrosis factor receptor-1 in said sample;

c) comparing the concentration of soluble tumor necrosis factor receptor-1 in said sample to an established baseline concentration of soluble tumor necrosis factor receptor-1, wherein a measured concentration of soluble tumor necrosis factor receptor-1 greater than said established baseline concentration is predictive of the presence of deep vein thrombosis in said patient; and d) predicting the presence of or development of deep vein thrombosis in said patient if the concentration of soluble tumor necrosis factor receptor-1 in said sample is greater than said established baseline concentration of soluble tumor necrosis factor receptor-1, wherein said established baseline concentration of soluble tumor necrosis factor receptor-1 is 1000 picograms/milliliter of venous blood.

* * * * *